United States Patent [19]

Murtha

[11] 4,055,567
[45] Oct. 25, 1977

[54] PREPARATION OF O,O'-DIHYDROXYAZOBENZENES FROM O-NITROPHENOLS

[75] Inventor: Timothy P. Murtha, Bartlesville, Okla.

[73] Assignee: Phillips Petroleum Company, Bartlesville, Okla.

[21] Appl. No.: 664,845

[22] Filed: Mar. 8, 1976

Related U.S. Application Data

[63] Continuation of Ser. No. 402,338, Oct. 1, 1973, abandoned.

[51] Int. Cl.$^2$ .................... C09B 27/00; C09B 43/00
[52] U.S. Cl. .................................. 260/206; 260/207
[58] Field of Search ............................... 260/206, 207

[56] References Cited
PUBLICATIONS

Brand & Schreber, *Ber.* 75. 1942, pp. 156–165.

Wagner & Zook, *Synthetic Organic Chemistry*, John Wiley & Sons, Inc., New York, 1953, pp. 765–766. Ibid., at pp. 171–172.

*Primary Examiner*—Charles E. Warren

[57] ABSTRACT

Compounds having the formula

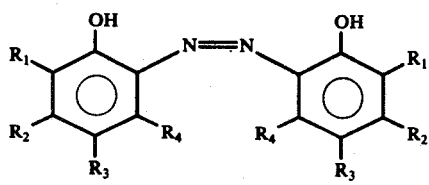

are prepared from a corresponding o-nitrophenol by blocking the hydroxyl groups via acetal formation, followed by reductive coupling and acid hydrolysis.

18 Claims, No Drawings

PREPARATION OF O,O'-DIHYDROXYAZOBENZENES FROM O-NITROPHENOLS

This is a continuation of my copending application Ser. No. 402,338, filed Oct. 1, 1973, now abandoned.

This invention relates to the preparation of an o,o'-dihydroxyazobenzene. In one of its aspects, it relates to the preparation of such a compound from an o-nitrophenol.

In one of its concepts, the invention provides a process for producing an o,o'-dihydroxyazobenzene from an o-nitrophenol by blocking the hydroxyl group as an acetal, followed by reductive coupling to the corresponding azobenzene and acid hydrolysis to regenerate the hydroxyl groups of the product thus obtained.

It has now occurred to me that compounds having the formula:

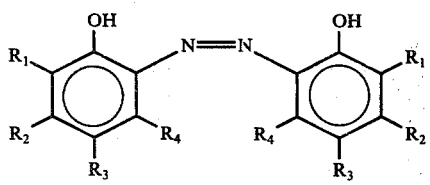

can be readily prepared from the corresponding o-nitrophenol by first blocking the hydroxyl functions via acetal formation, then reductively coupling to the corresponding azobenzene followed by acid hydrolysis to regenerate the hydroxyl groups.

Thus, compounds of the above formula, such as 2,2'-dihydroxy-5,5'-bis (1,1,3,3-tetramethylbutyl) azobenzene ($R_1 = R_2 = R_4 = H$; $R_3 = 1,1,3,3$-tetramethylbutyl), are prepared from the corresponding o-nitrophenol. Compounds which are to be included as useful in this invention are those with a variety of substituents (the various R's being hydrogen, alkyl, aryl, cycloalkyl, and combinations thereof such as alkaryl and aralkyl, alkoxy, aryloxy, tert-amino, alkylthio, etc., containing up to about 12 carbon atoms and being either alike or different). Examples of specific R groups which can be employed are hydrogen, methyl, ethyl, tert-butyl, 1,1,3,3-tetramethylbutyl, n-dodecyl, cyclohexyl, phenyl, p-tolyl, benzyl, n-butoxy, phenoxy, dimethylamino, n-propylthio, etc. Hydrocarbyl radicals are presently preferred. Compounds of formula I are well known in the art to be useful as dyestuffs and also as ultraviolet stabilizers for polymers.

It is an object of this invention to provide a process for the preparation of o,o'-dihydroxyazobenzenes. It is another object of this invention to provide such compounds from o-nitrophenols. It is a further object of this invention to provide a process for the production of compounds as herein described involving several synthesis steps.

Other aspects, concepts, objects, and the several advantages of this invention are apparent from a study of this disclosure and the appended claims.

According to the present invention, an o,o'-dihydroxyazobenzene is prepared from a corresponding o-nitrophenol by first blocking the hydroxyl function of the nitrophenol via acetal formation, then reductively coupling to the corresponding azobenzene followed by acid hydrolysis to regenerate the hydroxyl groups of the compound thus obtained.

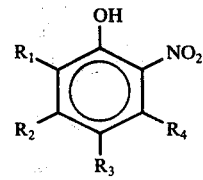

Compounds of formula II above, such as 2-nitro-4-(1,1,3,3-tetramethylbutyl)phenol (II with $R_1 = R_2 = R_4 = H$; $R_3 = 1,1,3,3$-tetramethylbutyl), can be used as starting materials in this invention. The R's can generally be as defined above. If not otherwise obtainable, these compounds can be prepared by nitration of the corresponding phenol or oxidation of the corresponding o-aminophenol using well-known methods.

The following reaction scheme illustrates the blocking of the hydroxyl group of II.

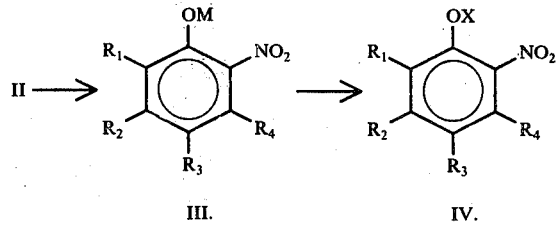

Blocking of the hydroxyl group of II as an acetal is accomplished by one of several known methods. Conversion of II to the metal salt III (M is preferably an alkali metal, such as sodium, potassium, etc.) and reaction of III with chloromethyl methylether to give the acetal IV (X - methoxymethyl) provides a convenient means of blocking the hydroxyl group of II. Other groups such as methyl ethers, benzyl ethers, trimethylsilyl ethers, tetrahydropyranyl ethers, acetates, benzoates, etc. which effectively block the hydroxyl function of II and which can be easily removed following the coupling step are within the scope of this invention.

The conversion of the nitrophenol compound II to the alkali metal salt III can be carried out by any suitable method such as by reacting II with a suitable alkali metal base, such as sodium methoxide, under conditions of time and temperature which are sufficient to substantially convert II to the metal salt.

The conversion of the salt III to the acetal derivative IV can be carried out by any suitable method such as by reacting a suitable acetal-forming compound such as chloromethyl methyl ether with III under conditions of time and temperature which are sufficient to produce a substantial quantity of the acetal compound IV. If desired, an acid acceptor such as potassium carbonate can be present in this step.

Reaction temperatures for this blocking step of the process are generally in the approximate range 0°-50° C, but the range 10°-35° C is preferable.

Volatile alcohols, such as methanol, ethanol, isopropanol, etc., are preferred solvents for preparation of III. Preferred solvents for preparation of IV include paraffins, cycloparaffins, aromatics, ketones, ethers, thioethers, and the like. Acetone is most preferred.

Reductive coupling of nitro-substituted acetals, such as IV, to give the corresponding azobenzenes, such as V, is acomplished.

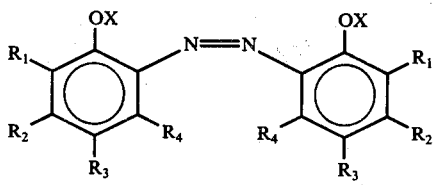

according to known procedures using strong reducing agents such as lithium aluminum hydride, sodium aluminum diethyl dihydride, sodium borohydride, and the like. Ethers, such as diethyl ether, are preferred solvents.

Thus, the acetal IV can be reacted with a strong reducing agent, such as lithium aluminum hydride, in a suitable solvent such as diethyl ether, under conditions of time and temperature sufficient to substantially convert the acetal IV to the reductively coupled product V.

The reaction can be carried out at temperatures of from about 0° to about 50° C, though from about 10° to about 35° C is preferred.

Mild acid hydrolysis of the coupled products, such as V, cleaves the acetal groups and regenerates the hydroxy groups leaving the desired product of formula I.

Thus, the final hydrolysis step can be carried out using any suitable method such as by contact, under reaction conditions, with a dilute aqueous solution of a mineral acid, such as dilute hydrochloric acid, under conditions of time and temperature suitable to produce the desired azobenzene compound I.

If reductive coupling of II is attempted as described above, but without first blocking the hydroxy groups, no coupled product, i.e., substituted azobenzenes, are observed. The corresponding o-aminophenol is the major product.

The final product, as well as intermediate products, can be separated and isolated, if desired, using suitable separation techniques which are well known in this art. For example, suitable separations are made by evaporation, filtration, crystallization, extraction and the like.

EXAMPLE I

A substituted 2,2'-dihydroxyazobenzene was prepared according to the following procedure. 67.4 parts of 2-nitro-4-(1,1,3,3-tetramethylbutyl)-phenol was added rapidly to a stirred suspension of 29.2 parts of sodium methoxide in 555 parts methyl alcohol at ambient temperature. After continued stirring for 30 minutes the methyl alcohol was removed by evaporation under reduced pressure. The residue was treated with 277 parts of acetone and filtered to remove excess sodium methoxide.

7.0 parts of potassium carbonate was suspended in the acetone solution. Over a 30-minute period at ambient temperature 2.72 parts of freshly distilled chloromethyl methylether was added dropwise to the stirred suspension. During addition of the ether the temperature increased to about 35° C. One additional hour of stirrng followed by filtration and distillation yielded 51.3 parts (64.5% of theory) of 2-nitro-4-(1,1,3,3-tetramethylbutyl)phenyl methoxymethyl ether: b.p. 149°–151° C (0.07 torr); important ir bands (neat) 1550 and 1360 (nitro), 985 and 930 (ether) cm.$^{-1}$ 5.15 parts lithium aluminum hydride (as a 3.9 molar solution in diethyl ether) and 57 parts diethyl ether were mixed and cooled in an ice bath to 18° C. A solution of 20 parts 2-nitro-4-(1,1,3,3-tetramethylbutyl)-phenyl methoxymethyl ether in 28.5 parts diethyl ether was added dropwise with continuous stirring over a 30-minute period. By regulating rate of the addition and cooling with an ice bath the temperature of the reaction solution was maintained at 9°–12° C. After addition was complete the solution was allowed to stand at ambient temperature for 90 minutes. After cooling to 0° C, 25 parts water were added slowly to decompose excess lithium aluminum hydride. Filtration removed aluminum hydroxide after which extraction of the filtrate with ether and subsequent removal of ether by evaporation left 17.8 parts of red liquid containing 2,2'-bis(methoxy methyl ether) of 2,2'-dihydroxy-5,5'-bis (1,1,3,3-tetramethylbutyl)azobenzene.

To a solution of the red liquid in 67 parts ethyl alcohol were added four parts water and four parts concentrated hydrochloric acid. After refluxing for 1 hour, cooling the dark solution yielded 3.9 parts (27 percent of theoretical yield from nitroacetal) needle-like crystals of 2,2'-dihydroxy-5,5'-bis(1,1,3,3-tetramethylbutyl)azobenzene: m.p. 159°–162° C recrystallized from ethanol; important ir bands (KBr), 3550 (hydroxyl), 1640 (azo) and 1610 (aromatic) cm.$^{-1}$

EXAMPLE II

The substituted 2,2'-dihydroxyazobenzene prepared in Example I was also prepared by a known independent synthesis to verify the identity of the final product and to compare to the process of the instant invention.

Diazotization of 2-amino-4-(1,1,3,3-tetramethylbutyl)phenol using sodium nitrite gave the corresponding diazonium salt which was coupled using a solution of copper (I) complex ions. 2,2'-dihydroxy-5,5'-bis(1,1,3,3-tetramethylbutyl)azobenzene was obtained in nine percent yield (based on starting aminophenol).

EXAMPLE III

Attempted coupling of 2-nitro-4-(1,1,3,3-tetramethylbutyl)phenol without first blocking the hydroxy group as in Example I is described in the following procedure. A solution of 36 parts diethyl ether and 4.0 parts lithium aluminum hydride (as a 3.9 molar solution in ether) was cooled to 15° C. To this continuously stirred solution was added dropwise over a one-hour period a solution of 7.54 parts 2-nitro-4-(1,1,3,3-tetramethylbutyl)phenol in 18 parts diethyl ether. The red solution was allowed to warm to ambient temperature for two hours after which 10 parts water was added to destroy the remaining lithium aluminum hydride. Addition of a 10 percent (by weight) solution of sulfuric acid and water gave 6.9 parts of a white precipitate which upon dissolving in methanol and subsequent treatment with concentrated ammonium hydroxide saturated with sodium sulfite and also treatment with sodium hydrogen sulfite gave 4.6 parts of a white solid (m.p. 130°–132° C; 70 percent of theoretical yield) identified as 2-amino-4-(1,1,3,3-tetramethylbutyl)phenol. Therefore, absence of a blocking group on the hydroxyl function lead predominantly to reduction of the nitro group to a primary amine rather than to reductive coupling to the azobenzene compound described in Example I and no coupled products were observable.

Non-limiting examples of compounds which can be prepared by means of my invention include the following: 2,2'-dihydroxyazobenzene; 4,4'-diethyl-2,2'-dihydroxyazobenzene; 2,2'-dihydroxy-5,5'-bis(1,1,3,3-tetramethylbutyl) azobenzene; 3,3'-dicyclohexyl-5,5'-di-n-dodecyl-2,2'-dihydroxyazobenzene; 2,2'-dihydroxy-4,4'-di-p-tolylazobenzene; 5,5'-di-n-butoxy-2,2'-dihydroxy-3,3'-dimethylazobenzene; 2,2'-dihydroxy-4,4'-bis(dimethylamino)azobenzene; 2,2'-dihydroxy-6,6'-di-n-propylthio azobenzene; and the like.

Reasonable variation and modification are possible within the scope of the foregoing disclosure and the appended claims to the invention the essence of which is that o,o'-dihydroxyazobenzenes are prepared from corresponding o-nitrophenols by first blocking the hydroxyl functions via acetal formation, then reductively coupling the blocked compound to the corresponding azobenzene followed by acid hydrolysis to regenerate the hydroxyl groups.

What is claimed is:

1. A process for the preparation of an o,o'-dihydroxyazobenzene having the following formula

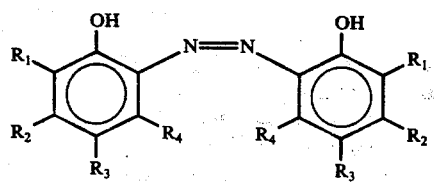
I.

wherein the R's are individually selected from the group consisting of hydrogen, alkyl, aryl, cycloalkyl, alkaryl, aralkyl, alkoxy, aryloxy, tert-amino, and alkylthio, said R's containing up to about 12 carbon atoms, which comprises 1. forming an acetal of an o-nitrophenol of the formula:

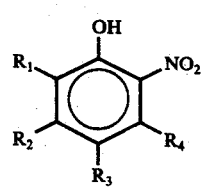
II.

wherein the R's are as earlier stated,
2. reacting said acetal with a reducing agent under such conditions that said acetal is converted to the corresponding diacetal azobenzene, and
3. then employing acid hydrolysis upon said diacetal azobenzene to regenerate the hydroxyl groups and yield the corresponding o,o'-dihydroxyazobenzene.

2. A process according to claim 1 wherein R's are individually selected from the group consisting of hydrogen; methyl; ethyl; tert-butyl; 1,1,3,3-tetramethylbutyl; n-dodecyl; cyclohexyl; phenyl; p-tolyl; benzyl; n-butoxy; phenoxy; dimethylamino; and n-propylthio.

3. A process according to claim 1 wherein $R_1$, $R_2$ and $R_4$ are hydrogen and $R_3$ is a hydrocarbyl radical.

4. A process according to claim 1 wherein said o,o'-dihydroxyazobenzene that is prepared is selected from the group consisting of 2,2'-dihydroxyazobenzene; 4,4'-diethyl-2,2'-dihydroxyazobenzene; 2,2'-dihydroxy-5,5'-bis(1,1,3,3-tetramethylbutyl)azobenzene; 3,3'-dicyclohexyl-5,5'-di-n-dodecyl-2,2'-dihydroxyazobenzene; 2,2'-dihydroxy-4,4'-di-p-tolylazobenzene; 5,5'-di-n-butoxy-2,2'-dihydroxy-3,3'-dimethylazobenzene; 2,2'-dihydroxy-4,4'-bis(dimethylamino)azobenzene; and 2,2'-dihydroxy-6,6'-di-n-propylthioazobenzene.

5. A process according to claim 1 wherein the reducing agent is selected from the group consisting of lithium aluminum hydride, sodium aluminum diethyl dihydride, and sodium borohydride.

6. A process according to claim 5 wherein said acetal is reacted with said reducing agent in the presence of a suitable solvent and at a temperature in the range of about 0° to about 50° C.

7. A process according to claim 6 wherein said reducing agent consists of lithium aluminum hydride.

8. A process according to claim 7 wherein said solvent comprises diethyl ether and said acetal is reacted with said reducing agent at a temperature in the range of about 10° to about 35° C.

9. A process for the preparation of 2,2'-dihydroxy-5,5'-bis-(1,1,3,3-tetramethylbutyl)azobenzene comprising 1. forming an acetal of 2-nitro-4-(1,1,3,3-tetramethylbutyl)phenol,
2. reacting said acetal with a reducing agent selected from the group consisting of lithium aluminum hydride, sodium aluminum diethyl dihydride, and sodium borohydride under conditions sufficient to produce the corresponding diacetal azobenzene; and
3. employing acid hydrolysis upon said diacetal azobenzene to regenerate the hydroxyl groups and yield the corresponding dihydroxy azobenzene.

10. A process according to claim 9 wherein said acetal is reacted with said reducing agent in a suitable solvent.

11. A process according to claim 10 wherein said acetal is reacted with said reducing agent at a temperature in the range of about 0° to about 50° C.

12. A process according to claim 11 wherein said reducing agent consists of lithium aluminum hydride.

13. A process according to claim 12 wherein said solvent comprises diethyl ether and said acetal is reacted with said reducing agent at a temperature in the range of about 10° to about 35° C.

14. A process according to claim 13 wherein said acetal is the methoxymethyl ether of 2-nitro-4-(1,1,3,3-tetramethylbutyl)phenol.

15. A process for the preparation of an o,o'-dihydroxyazobenzene having the formula

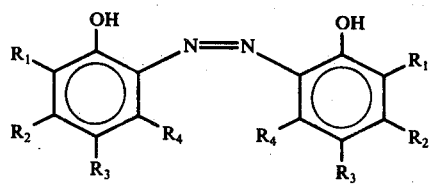
I.

wherein the R's are individually selected from the group consisting of hydrogen and hydrocarbyl, said R's containing up to about 12 carbon atoms, which comprises 1. forming an acetal of an o-nitrophenol of the formula:

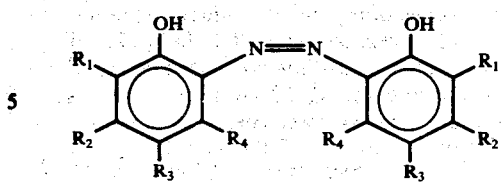

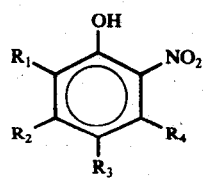

wherein the R's are as earlier stated, 2. reacting said acetal with a reducing agent under such conditions that said acetal is converted to the corresponding diacetal azobenzene, and 3. then employing acid hydrolysis upon said diacetal azobenzene to regenerate the hydroxyl groups and yield the corresponding o,o'-dihydroxyazobenzene.

16. A process according to claim 15 wherein $R_1$, $R_2$, and $R_4$ are hydrogen and $R_3$ is a hydrocarbyl radical.

17. A process according to claim 16 wherein said reducing agent consists of lithium aluminum hydride and said acetal is reacted with said reducing agent in the presence of a suitable solvent and at a temperature in the range of about 0° to about 50° C.

18. A process for the preparation of an o,o'-dihydroxyazobenzene having the following formula wherein the R's are individually selected from the group consisting of hydrogen, alkyl, aryl, cycloalkyl, alkaryl, aralkyl, alkoxy, aryloxy, tert-amino, and alkylthio, said R's containing up to about 12 carbon atoms, which consists essentially of 1. forming an acetal of an o-nitrophenol of the formula:

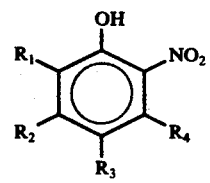

wherein the R's are as earlier stated, 2. reacting said acetal with a reducing agent under such conditions that said acetal is converted to the corresponding diacetal azobenzene, and 3. then employing acid hydrolysis upon said diacetal azobenzene to regenerate the hydroxyl groups and yield the corresponding o,o'-dihydroxyazobenzene.

* * * * *